US012648981B1

(12) United States Patent
    Alkhuriji et al.

(10) Patent No.: US 12,648,981 B1
(45) Date of Patent: Jun. 9, 2026

(54) *ACACIA NILOTICA* BASED HYDROGEL AND METHOD OF MAKING THE SAME

(71) Applicant: KING SAUD UNIVERSITY, Riyadh (SA)

(72) Inventors: Afrah Fahad Alkhuriji, Riyadh (SA);
              Manal Ahmed Awad, Riyadh (SA);
              Hayat Saeed Althobaiti, Riyadh (SA);
              Khalid Mustafa Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/352,450

(22) Filed: Oct. 7, 2025

(51) Int. Cl.
    *A61K 36/00*     (2006.01)
    *A61K 9/06*      (2006.01)
    *A61K 36/48*     (2006.01)
    *A61K 47/10*     (2017.01)
    *A61K 47/12*     (2006.01)
    *A61K 47/36*     (2006.01)
    *A61P 17/02*     (2006.01)

(52) U.S. Cl.
    CPC ................ *A61K 36/48* (2013.01); *A61K 9/06*
        (2013.01); *A61K 47/10* (2013.01); *A61K 47/12*
        (2013.01); *A61K 47/36* (2013.01); *A61P 17/02*
                                                    (2018.01)

(58) Field of Classification Search
    CPC ..................................................... A61K 36/48
    See application file for complete search history.

(56)                    References Cited

U.S. PATENT DOCUMENTS

2022/0305170 A1     9/2022   Tanaka et al.

FOREIGN PATENT DOCUMENTS

CN         115093580 B      2/2025

OTHER PUBLICATIONS

Yousif, Miriam Fouad, M. Haider, and A. A. Sleem. "Formulation and evaluation of two anti-inflammatory herbal gels." Journal of Biologically Active Products from Nature 1.3 (2011): 200-209.
Elblbesy, Mohamed A., Taha A. Hanafy, and Mamdouh M. Shawki. "Polyvinyl alcohol/gum arabic hydrogel preparation and cytotoxicity forwound healing improvement." e-Polymers 22.1 (2022): 566-576.
Yao, Fanglian, et al. "A novel amphoteric, pH-sensitive, biodegradable poly [chitosan-g-(l-lactic-co-citric) acid] hydrogel." Journal of applied polymer science 89.14 (2003): 3850-3854.

*Primary Examiner* — Qiuwen Mi
(74) *Attorney, Agent, or Firm* — Nath, Goldberg & Meyer; Joshua B. Goldberg

(57)                    ABSTRACT

An *Acacia nilotica* based hydrogel may include chitosan in a 1% lactic acid solution, glycerol in distilled water, and *Acacia nilotica*. The *Acacia nilotica* may be an active ingredient. A method of treating wounds may include using the *Acacia nilotica*-based hydrogel. The *Acacia nilotica*-based hydrogel may be made by dissolving chitosan in a lactic acid solution to obtain a mixture, adding glycerol in distilled water to the mixture to obtain a second mixture, stirring the second mixture continuously to obtain a homogeneous hydrogel, and adding *Acacia nilotica* powder to the homogeneous hydrogel to obtain a wound healing hydrogel.

4 Claims, 6 Drawing Sheets

ACACIA NILOTICA BASED HYDROGEL AND METHOD OF MAKING THE SAME

BACKGROUND OF THE INVENTION

Field of the Invention

The disclosure of the present patent application relates to wound treatment and, particularly, to an *Acacia nilotica* based hydrogel for healing wounds in patients with diabetes.

Description of Related Art

Wound healing is a critical biological process that involves a series of complex cellular and molecular mechanisms aimed at tissue regeneration and repair. Traditional wound care treatments often face limitations such as infection risk, slow healing rates, and poor moisture retention. In recent years, natural-based hydrogels have gained attention due to their biocompatibility, biodegradability, and ability to provide a moist healing environment.

*Acacia nilotica*, a medicinal plant rich in polyphenols, flavonoids, and tannins, has been widely recognized for its antibacterial, anti-inflammatory, and antioxidant properties, making it an excellent candidate for wound healing applications.

Thus, wound treatments that are natural, cost-effective, efficient and promote faster healing while reducing the risk of infections, are desirable.

SUMMARY OF THE INVENTION

Wound healing is a complex biological process involving cellular migration, inflammation, tissue regeneration, and remodeling. Effective treatment strategies are essential to accelerate healing, promote tissue regeneration, and prevent infections. The present disclosure relates to synthesizing an *Acacia nilotica*-based hydrogel for enhanced wound healing. *Acacia nilotica* is known for its abundance of bioactive compounds, including polyphenols, flavonoids, and tannins, possess antimicrobial, anti-inflammatory, and antioxidant properties. These attributes make it an excellent candidate for incorporation into a hydrogel matrix to develop a biocompatible and efficient wound dressing or gel formulation.

The present disclosure relates to a hydrogel including chitosan in a 1% lactic acid solution, glycerol in distilled water; and *Acacia nilotica*. The *Acacia nilotica* is an active ingredient in the hydrogel.

The present disclosure also relates to a method of treating wounds using the hydrogel including *Acacia nilotica*.

In an embodiment, the present disclosure relates to a method of making the hydrogel including *Acacia nilotica*. The method includes dissolving chitosan in a lactic acid solution to obtain a mixture, adding glycerol in distilled water to the mixture to obtain a second mixture, stirring the second mixture continuously to obtain a homogeneous hydrogel, then adding *Acacia nilotica* powder to the homogeneous hydrogel to obtain a wound healing hydrogel.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Definitions

Figure 1A:
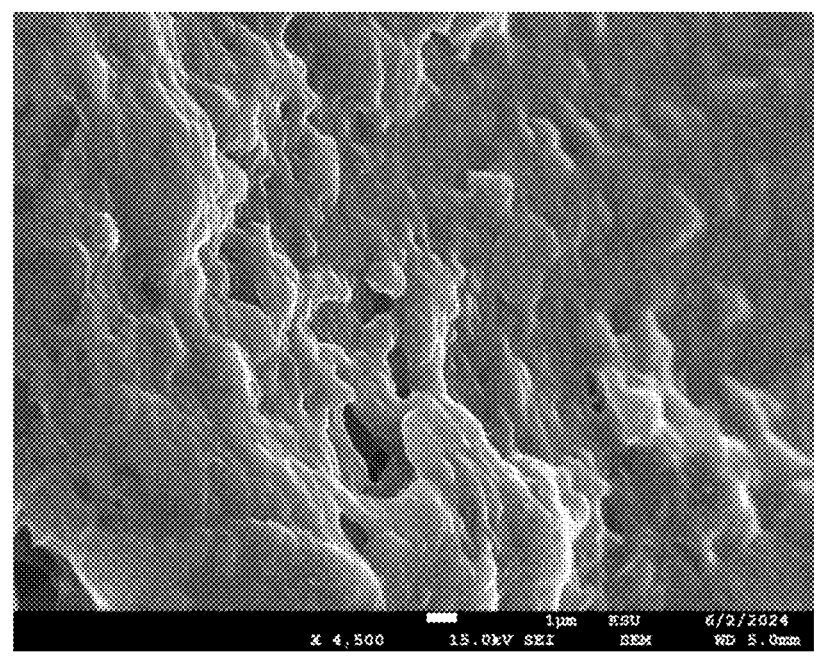
FIGS. 1A, 1B, and 1C are SEM images of embodiments of *Acacia nilotica* hydrogel.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present disclosure relates to an *Acacia nilotica* based hydrogel. The hydrogel may include chitosan in a 1% lactic acid solution, glycerol in distilled water, and *Acacia nilotica*. The *Acacia nilotica* may be an active ingredient.

In various embodiments, the hydrogel may include at least about 2 g chitosan, at least 2 g chitosan, or about 2 g chitosan.

In some embodiments, the hydrogel may include at least about 2 mL glycerol, at least 2 mL glycerol, or about 2 mL glycerol.

In other embodiments, the hydrogel may include at least about 1 g *Acacia nilotica*, at least 1 g *Acacia nilotica*, or about 1 g *Acacia nilotica*. The *Acacia nilotica* may also be known as *Acacia nilotica*.

In an embodiment, a method of treating a wound using the *Acacia nilotica* hydrogel includes applying, e.g., topically applying, the *Acacia nilotica* hydrogel to the wound.

An exemplary embodiment for preparing an *Acacia nilotica* hydrogel may include dissolving chitosan in a lactic acid solution to obtain a mixture, adding glycerol in distilled water to the mixture to obtain a second mixture, stirring the second mixture continuously to obtain a homogeneous hydrogel, then adding *Acacia nilotica* powder to the homogeneous hydrogel to obtain a wound healing hydrogel. In various embodiments, 2 g of chitosan may be dissolved in a 1% lactic acid solution. In some embodiments, 2 mL of glycerol may be in distilled water.

The method may further include placing the wound healing hydrogel in an ultrasonic bath to remove air bubbles.

In some embodiments, the hydrogel may be in the ultrasonic bath for at least about 2 hours.

In various embodiments, the stirring may include using a magnetic stirrer for at least about 5 hours, at least 5 hours, or about 5 hours.

In still other embodiments, the *Acacia nilotica* may be added under continuous stirring.

The present teachings are further illustrated in the following examples.

EXAMPLES

Example 1

Preparation of *Acacia nilotica* Based Hydrogel

Ten grams of *Acacia nilotica* with its husks were thoroughly washed under running tap water, air-dried, and then ground using an electric grinder. The ground material was sieved to obtain a fine powder, which was then stored for further use.

The hydrogel was formulated by dissolving 2 g of chitosan in a 1% lactic acid solution, followed by the addition of 2 mL of glycerol in distilled water. The mixture was stirred continuously using a magnetic stirrer for 5 hours to achieve a homogeneous hydrogel. Then, 1 g of *Acacia nilotica* powder was added to the chitosan hydrogel under continuous stirring until the *Acacia nilotica* was fully dispersed. The gel was then placed in an ultrasonic bath for 2 hours to remove any trapped air bubbles. The resulting hydrogel was characterized using various analytical techniques.

Figure 1B:
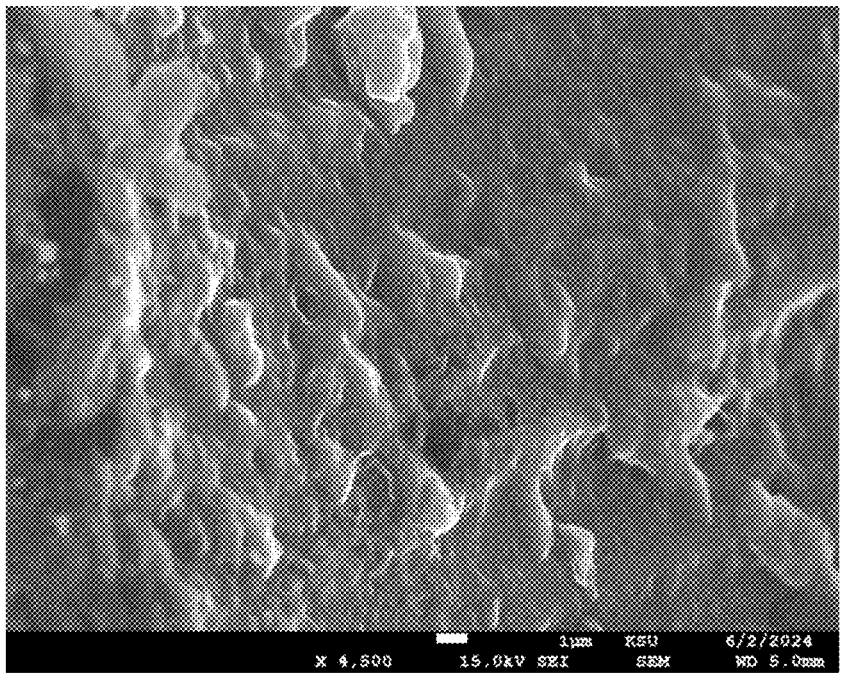
Figure 1C:
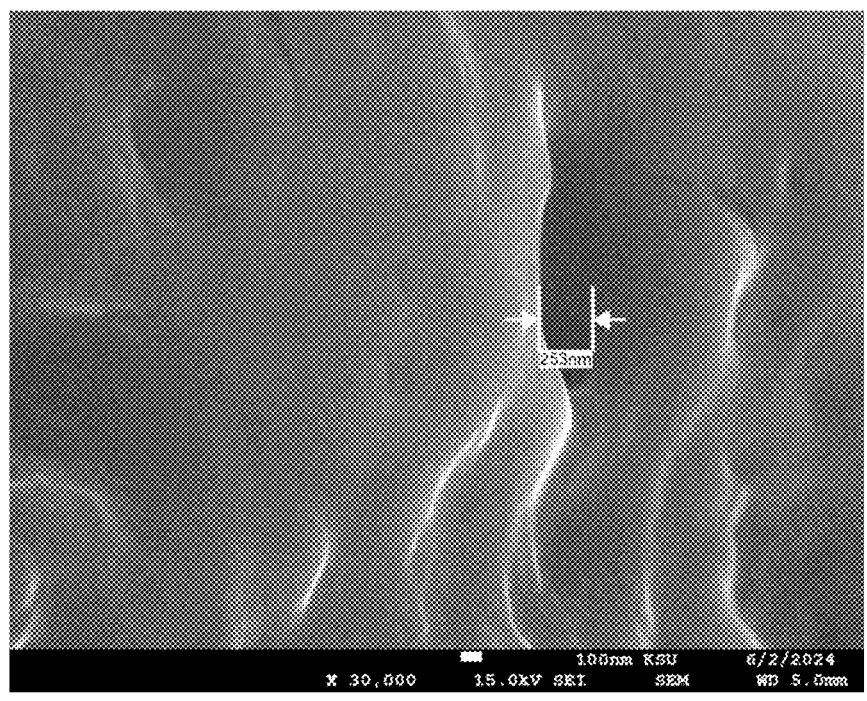
Figure 2:
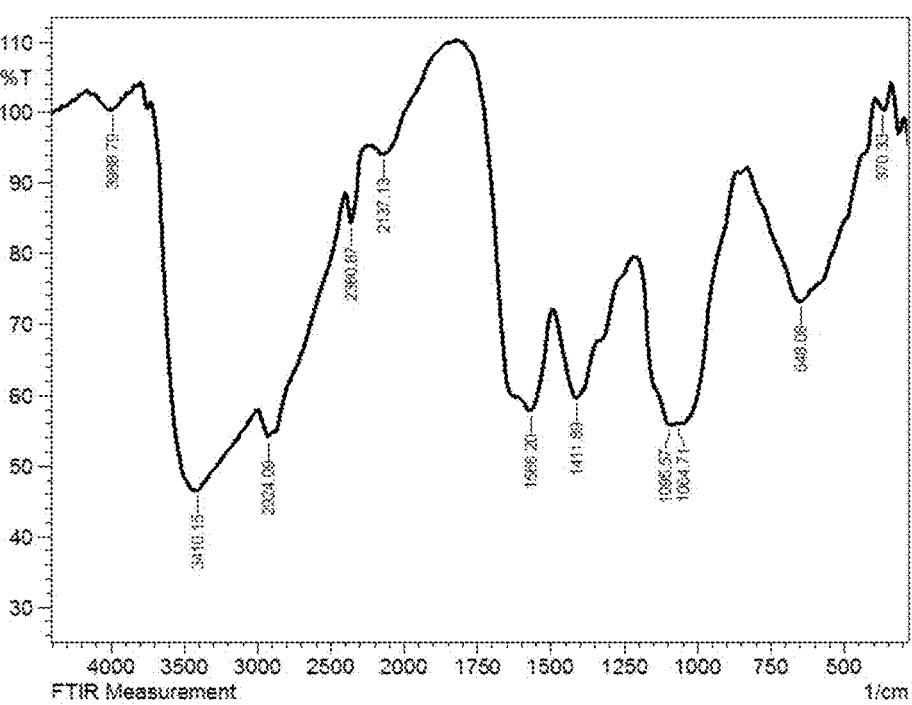
FIG. 2 is an FTIR analysis of a hydrogel not containing *Acacia nilotica*.
Figure 3:
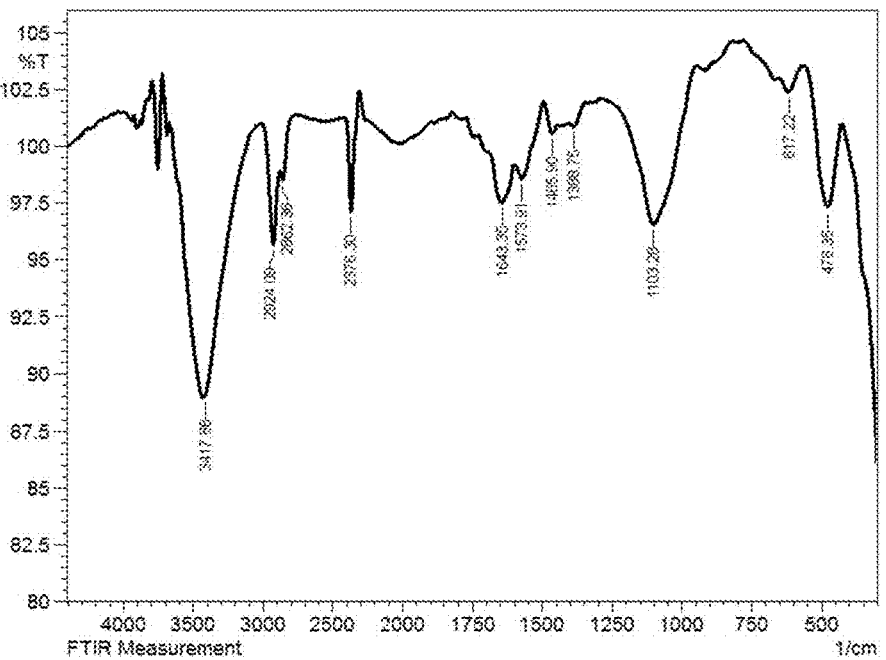
FIG. 3 is an FTIR analysis of an embodiment of a hydrogel containing *Acacia nilotica*.

Characterization of the hydrogel is illustrated in SEM images of embodiments of the *Acacia nilotica* hydrogel in FIG. 1A, 1B, or 1C.

Example 2

Experimental Animal Studies

The 32 Wistar albino male rats (200 g±30, 8-10 weeks old) were obtained from King Saud University, Riyadh.

The animals were housed in polycarbonate cages at 25±2° C. and 55-60% humidity under a 12-hour light/dark cycle.

Experimental Design

Diabetes type 2 induction Animals were fasted overnight. The following day, the rats were given an intraperitoneal injection (i.p.) of 50 mg/kg of StrepToZotocin (STZ) in freshly prepared citrate buffer (pH 4) for three constitutive days to induce hypercalcemia. STZ is an alkylating antineoplastic agent that is particularly toxic to the insulin-producing beta cells of the pancreas in mammals. The animals were left for 5 days, then fasting blood glucose levels were measured with a glucometer.

The blood was taken from the tail vein (while the animal was under anesthesia). Rats with blood glucose levels above 200 mg/dL were considered diabetic.

The diabetic rats were anesthetized using ether. Square diabetic wounds (2.25 cm$^2$ in area) were induced on the dorsal position of rats after shaving their skin hair. Then, the wounds were washed and cleaned using an ethanol solution (70%, v/v). Starting a day after surgery, the animals were randomly categorized into four groups (n=8). Forty (32) male Wistar albino rats were divided into six groups (n=8 per each), as follows: Group 1 (Control) rats stayed without any treatment and the wound was left uncovered for 17 days. The wound diameter was recorded every four days. Group 2 (saline) rats were treated with saline as another control. The saline was placed in pure cotton, the wet cotton was tied to the wound site with a bandage, and the cotton was replaced with the saline for a period of 17 days. The wound diameter was recorded every four days. Group 3 (commercial diabetic wound dressing) rats were treated with commercial bandages which were tied to the wound site, for a period of 17 days. The wound diameter was recorded every four days. Group 4 (*Acacia nilotica* hydrogel) rats were treated with *Acacia nilotica* hydrogel. The hydrogel was applied to the wound site, the wound site was tied with a bandage, and the hydrogel was replaced daily for a period of 17 days. The wound diameter was recorded every four days.

Finally, wounds were photographed on days 0, 3, 7, and 14. The wound areas were measured using Image J software.

Samples Collection

At the end of the experiment and after fasting, the animals were anesthetized, and blood was collected in two different tubes, i.e. one with EDTA and another without anticoagulant for serum separation. The blood was centrifuged at 3000 rpm for 20 minutes using a refrigerated centrifuge at 4° C. to separate the serum. Then, the animals were euthanized and their skins were collected immediately and cut into small pieces, fixed in 10% formalin, and subjected to a histological process.

Results

Figure 4:
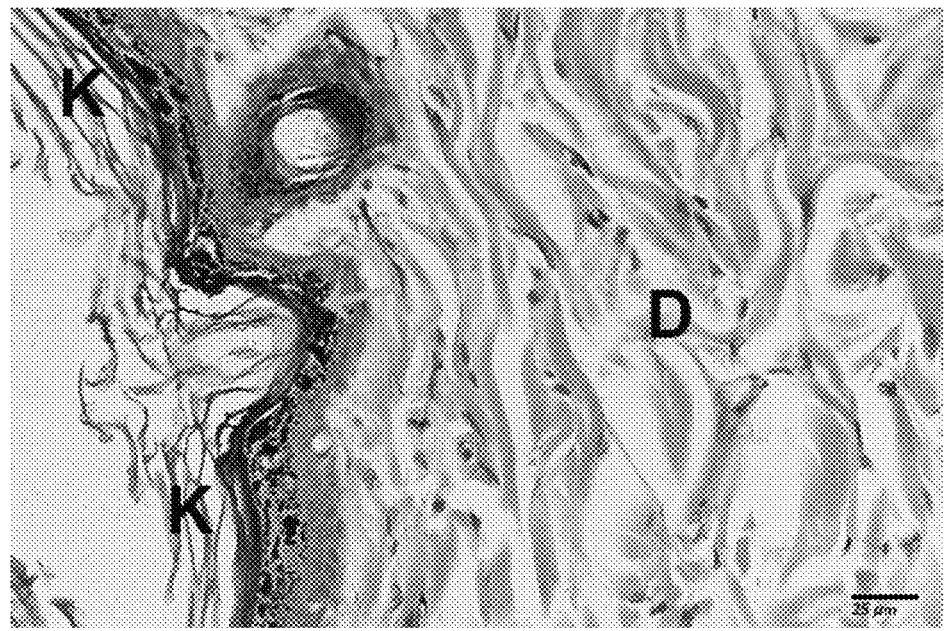
FIG. 4 is a photomicrograph of control skin showing normal skin.
Figure 5:
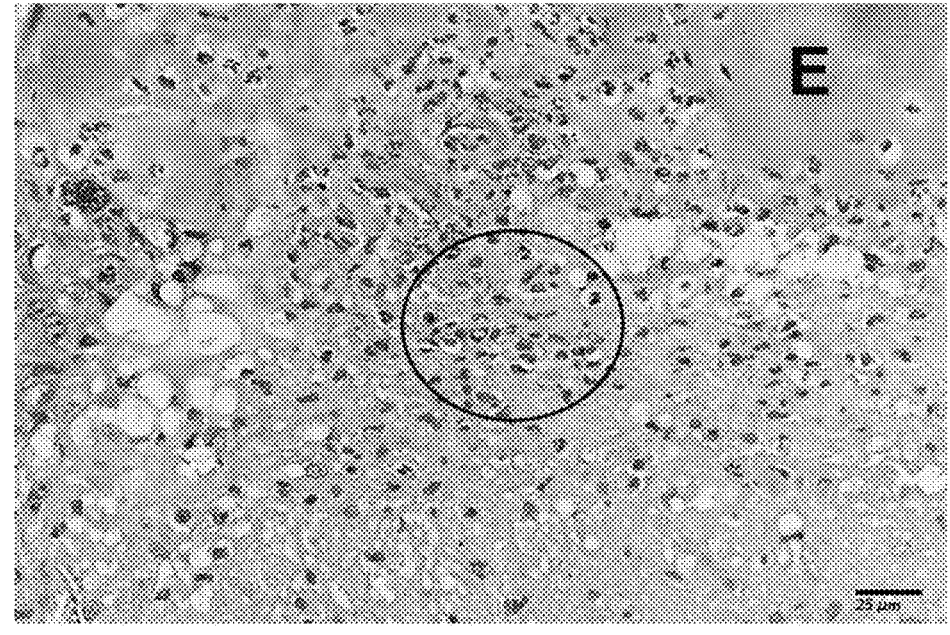
FIG. 5 is a photomicrograph of an untreated wound without epidermis.
Figure 6:
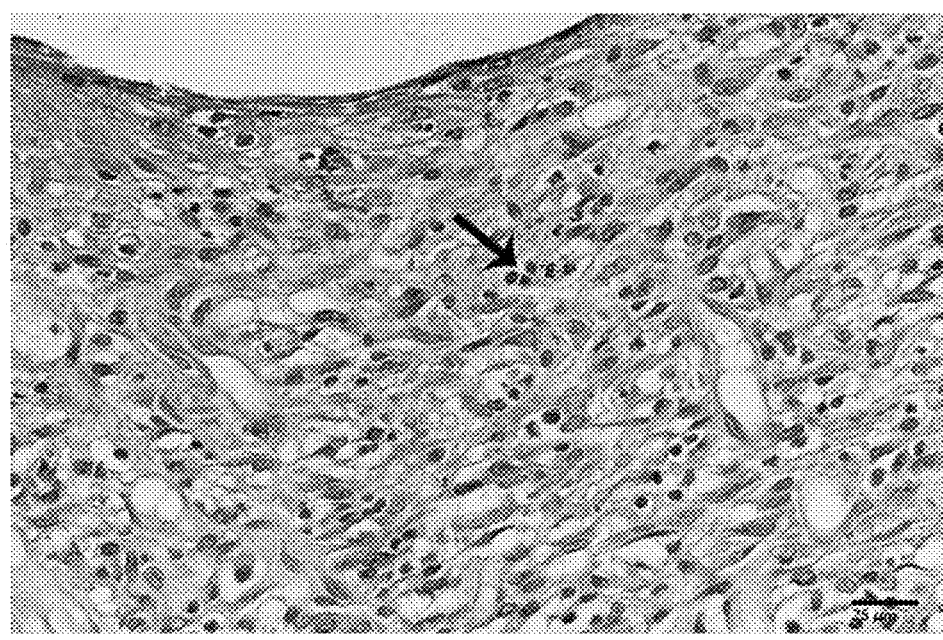
FIG. 6 is a photomicrograph of a wound covered with a bandage revealing.
Figure 7:
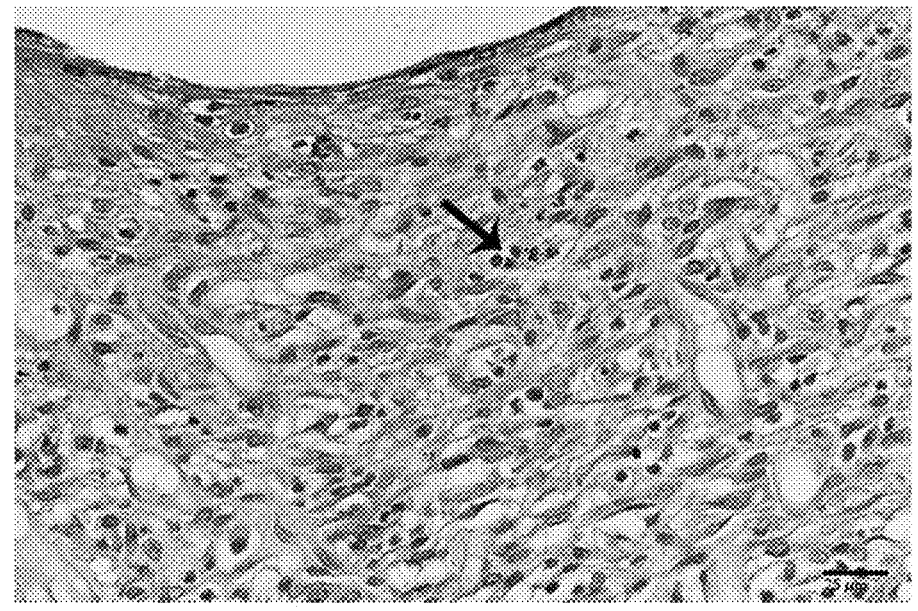
FIG. 7 is a photomicrograph of a wounded animal treated with an embodiment of a hydrogel containing *Acacia nilotica*.
Figure 8:
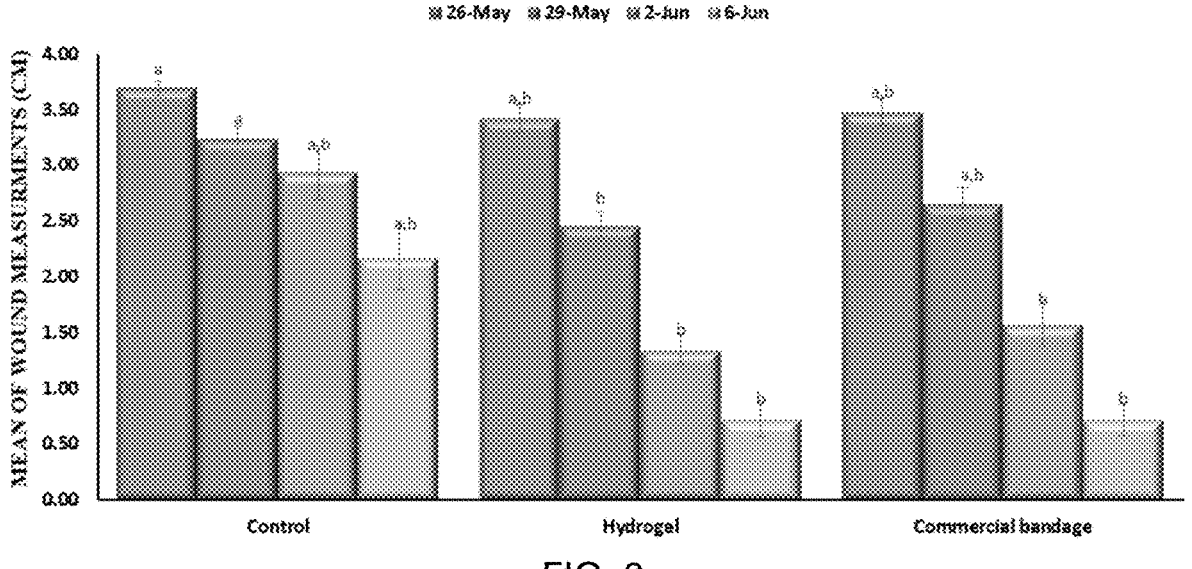
FIG. 8 is a graph illustrating wound size measurements after treatment with an embodiment of a hydrogel containing *Acacia nilotica*, wherein the letters "a" and "b" indicate statistical difference based upon Tukey's test.
Figure 9:
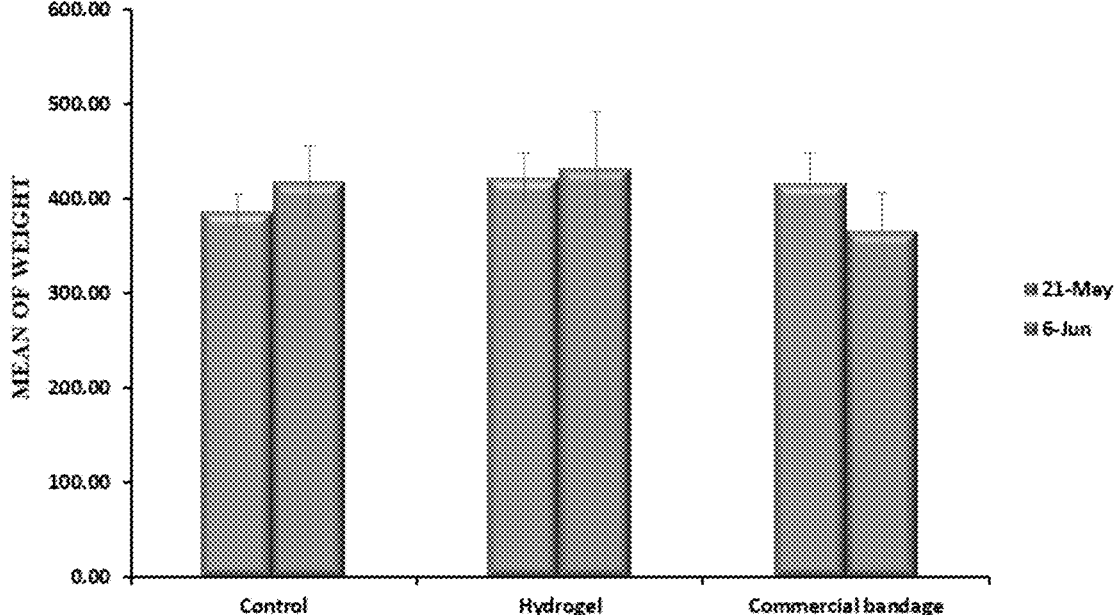
FIG. 9 is a graph illustrating animal weight measurements after treatment with an embodiment of a hydrogel containing *Acacia nilotica*.

Referring to FIG. 4, the control skin showed a normal view with a thin layer of epidermis covered with layers of keratin and normal dermis with old collagen. The photomicrograph of FIG. 4 illustrates control skin showing normal skin with thin layer of epidermis, *granulosum* (green arrow), keratinized layers (K), and dermis (D). Referring to FIG. 5, the untreated wound revealed no epidermis covered with edema and accumulation of infiltrative cells in edema besides dermis. The photomicrograph of FIG. 5 illustrates untreated wound without epidermis covered with edema (E), accumulation of infiltrative cells (circle). Referring to FIG. 6, the wound covered with a bandage showed no epithelia, dermis with new collagen filled with infiltrative cells. The photomicrograph of FIG. 6 illustrates a wound covered with bandage revealing no epidermis, dermis filled with scattered infiltrative cells (black arrow). Referring to FIG. 7, the wounds of animals treated with *Acacia nilotica* hydrogel showed marked wound cure manifested with thick newborn epithelia covered with born keratin. The photomicrograph of FIG. 7 illustrates a wound on an animal. The wound was treated with *Acacia nilotica* hydrogel and shows newborn epidermis (NE), new keratinized layer (K), dermis (D).

The hydrogel described herein may contribute to healthcare innovation, sustainability, and economic diversification, particularly in the fields of biotechnology and pharmaceutical research. The development of an *Acacia nilotica*-based hydrogel for wound healing supports the goal of advancing medical solutions and enhancing patient care. By utilizing *Acacia nilotica*, a plant naturally found in Saudi Arabia, the hydrogel promotes the use of indigenous and sustainable resources, reducing dependence on imported pharmaceuticals and fostering local production of biomaterials.

Additionally, the hydrogel offers a biodegradable and eco-friendly alternative to synthetic wound dressings, aligning with the commitment to sustainable healthcare solutions and environmental conservation.

From an economic perspective, the hydrogel can provide a cost-effective, efficient wound dressing, contributing to better wound care management, particularly for dentistry (such as: management of oral infections), wounds and diabetic ulcers.

It is to be understood that the hydrogel and method of making the hydrogel described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A hydrogel, comprising:
chitosan in a 1% lactic acid solution;
glycerol; and
*Acacia nilotica;*
wherein the *Acacia nilotica* is an active ingredient.

2. The hydrogel of claim 1, wherein the hydrogel comprises about 2 g chitosan.

3. The hydrogel of claim 1, wherein the hydrogel comprises about 2 mL glycerol.

4. The hydrogel of claim 1, wherein the hydrogel comprises about 1 g *Acacia nilotica.*

* * * * *